United States Patent [19]

Grau

[11] Patent Number: 4,801,684
[45] Date of Patent: Jan. 31, 1989

[54] PROCESS FOR OBTAINING INSULIN PRECURSORS FROM REACTION MIXTURES RESULTING FROM THE FOLDING OF INSULIN PRECURSORS FROM THE CORRESPONDING S-SULFONATES

[75] Inventor: Ulrich Grau, Hofheim am Taunus, Fed. Rep. of Germany

[73] Assignee: Hoechst Aktiengesellschaft, Frankfurt am Main, Fed. Rep. of Germany

[21] Appl. No.: 924,850
[22] PCT Filed: Jan. 11, 1986
[86] PCT No.: PCT/EP86/00008
§ 371 Date: Sep. 2, 1986
§ 102(e) Date: Sep. 2, 1986
[87] PCT Pub. No.: WO86/04335
PCT Pub. Date: Jul. 31, 1986

[30] Foreign Application Priority Data

Jan. 19, 1985 [DE] Fed. Rep. of Germany ....... 3501641

[51] Int. Cl.$^4$ ............................................. C07K 7/40
[52] U.S. Cl. .................... 530/303; 530/304; 530/305
[58] Field of Search ....................... 530/303, 304, 305; 514/3, 4

[56] References Cited

U.S. PATENT DOCUMENTS

4,421,685 12/1983 Chance et al. ...................... 530/303
4,430,266 2/1984 Frank ................................. 530/303
4,654,324 3/1987 Chance et al. ...................... 514/3 X
4,701,440 10/1987 Grau ................................... 514/3

FOREIGN PATENT DOCUMENTS

0021169 1/1981 European Pat. Off. .
0037255 10/1981 European Pat. Off. .
0037256 10/1981 European Pat. Off. .

OTHER PUBLICATIONS

Chem.-Abstracts, 181618h, (1982), Frank et al.
Chem.-Abstracts, 110370f (1982), Dahno et al.
Chem.-Abstracts, 220286z, Losse et al. (1981).
Chem.-Abstracts, 220291x, Naithani et al. (1981).
Tetrahedron Letters, No. 12 (1973), Robinson et al., pp. 1-4.
Chem.-Abstracts, 181617g, (1981), Chance et al.

Primary Examiner—Howard E. Schain
Attorney, Agent, or Firm—Finnegan, Henderson, Farabow, Garrett, & Dunner

[57] ABSTRACT

A process for the preparation of insulin precursors of the formula (I)

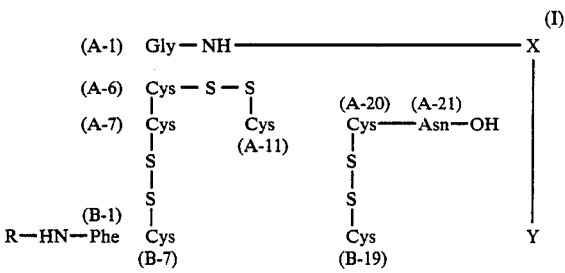

in which R is hydrogen or the presequence $P_m$—$Q_n$—, in which P is a sequence of naturally occurring amino acids with m being from 0 to 50, Q are basic natural amino acids, and n is an integer from 1 to 4, Y represents —Lys$^{B29}$—Z$^{B30}$—, in which Z denotes Ala, Thr or Ser, and the bridge extending from A-1 to A-21 is an insulin A-chain, the bridge extending from B-1 to B-30 represents an insulin B-chain, and X is a bridge which is bonded to the insulin A-chain at the amino group of A-1 and is bonded to the insulin B-chain at the ε-amino group of B-29— in which case it is bonded to the free bond of Z$^{B30}$OH— or at the carboxyl group of B-30, from reaction mixtures which result from folding of insulin precursors from S-sulfonates of the formula (II)

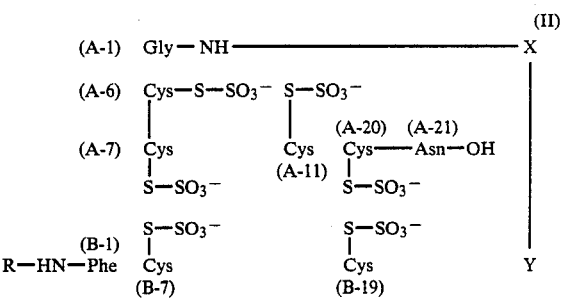

in which R, X and Y have the abovementioned meanings, which comprises the false recombinants contained in the reaction mixture being precipitated by adjustment of the reaction mixture to pH 4 to 6, the precipitate being removed in customary manner and converted by sulfitolysis into the S-sulfonate of the formula (II), and the latter then being subjected to renewed folding.

12 Claims, No Drawings

PROCESS FOR OBTAINING INSULIN PRECURSORS FROM REACTION MIXTURES RESULTING FROM THE FOLDING OF INSULIN PRECURSORS FROM THE CORRESPONDING S-SULFONATES

A process for the preparation of an insulin precursor of the formula I (see patent claim) is known, in which R is hydrogen, an amino acid residue which can be eliminated chemically or enzymatically, or a peptide residue which can be eliminated chemically or enzymatically and has at least two amino acid residues, Y represents —$Lys^{B29}$—$Z^{B30}$—, in which Z denotes Ala, Thr or Ser, the bridge extending from A-1 to A-21 being an insulin A-chain, the bridge extending from B-1 to B-30 representing an insulin B-chain, and X being a bridge which is bonded to the insulin A-chain at the amino group of A-1 and is bonded to the insulin B-chain at the carboxyl group of B-30, it being possible to cleave this bridge enzymatically or chemically without destroying the A-chain and the B-chain.

In this process, a S-sulfonate of the formula II (see patent claim 1), in which R, X and Y have the above-mentioned meanings, is reacted, in an aqueous medium at a pH of 7 to 11.5 and at a S-sulfonate concentration of up to 10 mg per ml of the aqueous medium, with a quantity of a mercaptan sufficient to result in 1–5 SH groups per $SSO_3^-$ unit (cf. European Pat. No. 37 255, corresponding to Japanese Published Specification No. 81-150051 and U.S. Pat. No. 4,430,266). The folding yield in this process depends on several parameters, such as pH, ratio of $SSO_3^-$ to —SH, the concentration, the nature of the mercaptan, the temperature and the reaction time. Under conditions approximating to those in practice, the process can be optimized to a folding yield of about 60%.

In other words, this entails the preparation of an insulin precursor by folding, with the formation of the natural spatial structure with three disulfide bridges, from which free insulin can then be obtained by subsequent transformation with proteases. During the conversion with the proteases, the falsely linked insulin precursors resulting as byproducts are broken down into fragments which cannot now be processed to give the desired insulin precursors with the aid of the same process. The term insulin precursors is defined in this context as both proinsulins and preproinsulins, the prefix "pre" being intended to relate to one or more additional amino acids on the N-terminal end of the proinsulin, and the proinsulin moiety itself preferably having the sequence of human or monkey proinsulin. Of course, in principle, other proinsulins are also possible, for example porcine, bovine or ovine, which can be isolated from pancreas, or those having synthetic sequences containing the human insulin sequence and being preparable by genetic engineering processes or, in the case of porcine insulin, being processable semi-synthetically to give human insulin.

It is known that not all the disulfide bridges in insulin are equally reactive, on the contrary there being, on mild reduction of the disulfide, initial opening of the disulfide bridge between cysteines A7 and B7 before the second disulfide bridge between cysteines B19 and A20 is opened. In our own investigations, the preferred reduction of the A7–B7 disulfide bridge was also observed on reaction of insulin precursor S-sulfonate with a small excess of mercaptan.

The further processing of the folded insulin precursor is carried out, according to the literature, with chromatographic processes, for example by removal of salts by gel chromatography, for example on $^{(R)}$Sephadex G 25, followed by gel chromatography on Sephadex G50 superfine, there being separation in the second stage of "aggregated forms" from natural insulin precursors.

It has now been found, surprisingly, that the false recombinants which result from the folding of insulin precursors from the corresponding S-sulfonates and whose contribution usually amounts to 30 to 50% of the quantity used can be precipitated directly from the folding medium at pH 4 to 6, while, in contrast, the natural form of the insulin precursor remains almost entirely in solution. This applies not only when about 2 equivalents of —SH are used per S-sulfonate group for the folding, but also when a somewhat larger quantity of mercaptan is used, which results in more extensive reduction to cysteine groups and thus in the formation of those insulin precursors which only partially contain disulfide bridges. The precipitate is then removed in a customary manner, for example by centrifugation, and is converted by sulfitolysis into the S-sulfonate of the formula II. The latter is then subjected once more to folding.

In the compounds of the formula I prepared according to the invention, R is hydrogen or an amino acid residue which can be eliminated chemically or enzymatically, or a peptide residue which can be eliminated chemically or enzymatically and has at least 2 amino acid residues of the formula $P_m$—$Q_n$—; in this, P is a sequence of naturally occurring amino acids with m from 0 to 50, and Q represents basic naturally occurring amino acids, in particular arginine or lysine, with n=1 to 4. $P_m$ can be, in particular, a part-sequence of β-galactosidase, it being possible for the relevant fragment $P_m$ to be directly expressed or produced only by cleavage with cyanogen bromide. Y represents —$Lys^{B-29}$—$Z^{B30}$—, in which Z denotes Ala, Thr or Ser; the bridge extending from A-1 to A-21 is an insulin A-chain, the bridge extending from B-1 to B-30 is an insulin B-chain, and X is a bridge which is bonded to the insulin A-chain at the amino group of A-1 and is bonded to the insulin B-chain at the ε-amino group of B-29—in which case it is bonded at the free bond of $Z^{B30}$ OH—or at the carboxyl group of B-30.

The process according to the invention now makes it possible to increase the overall folding yield in that the proportion of false recombinants is now no longer lost but is processed to give the desired insulin precursor in a straightforward process.

As has also been found, surprisingly, it is possible in a preferred embodiment to prevent the adsorption of naturally folded insulin precursors to the false recombinants if, before the precipitation, a small quantity of a physiologically acceptable, surface-active substance is added to the medium. Examples of suitable substances are polymers, i.e. homopolymers, copolymers or block polymers, of the formula $R^2$—O—$X_n$—$R^3$(III), in which $X_n$ is a chain of n members of the formula —CH($R^1$)—CH($R^1$)—O— (IV) in arbitrary sequence, n is 2 to 80, preferably 15 to 45, and $R^1$ is hydrogen, —$CH_3$ or —$C_2H_5$, it being possible for the radicals $R^1$ to be identical or different, and $R^2$ and $R^3$ being, independently of one another, hydrogen or an organic radical, but with the proviso that the compounds III contain at least 12 carbon atoms. Examples of possible meanings of $R^2$ and $R^3$ are alkyl having 1 to 20 carbon atoms, carboxyalkyl having 2 to 20 carbon atoms or alkylphenyl having 1 to 10 alkyl carbon atoms. Examples of radicals $R^2$ and $R^3$ are methoxy, ethoxy, propoxy, butoxy or the radicals derived from lauryl, myristyl or cetyl alcohol; carboxyalkyl groups derived from acetic, propionic, butyric, palmitic or stearic acid, nonylphenoxy, oleylamino or stearylamino.

$R^2$ or $R^3$ can also be derived from a polyhydric alcohol such as glycerol or pentaerythritol, or a polybasic carboxylic acid such as citric acid. Polyfunctional members $R^2$ or $R^3$ can be connected to two or more polyalkoxy chains of the abovementioned type, this resulting in branched products.

The abovementioned surface-active substances, which are generally added in an amount of 1 to 400, preferably 2 to 200, mg/l, can be prepared in customary manner by controlled addition of alkylene oxides onto alkylene polyglycols. The terminal hydroxyl groups can, where necessary, then be esterified or etherified.

It is also possible to use as surface-active substances phospholipids of the formula

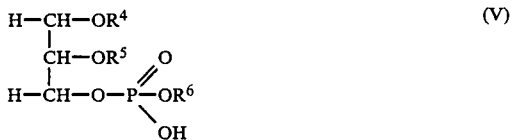

in which $R^4$ and $R^5$, which can be identical or different, represent alkylcarbonyl, alkenylcarbonyl, alkadienylcarbonyl or alkatrienylcarbonyl, each having 8 to 22, preferably 12 to 22, carbon atoms, or hydrogen, with the proviso that $R^4$ and $R^5$ are not both hydrogen, and in which $R^6$ represents a hydrophilic group. The concentration of these compounds is generally 1 to 20, preferably 1 to 10, in particular 2.5 to 7.5, % by weight. Examples of hydrophilic groups of this type are 2-(trimethylammonium)ethyl, 2-aminoethyl, 2-carboxy-2-aminoethyl, 2,3-dihydroxypropyl or 2,3,4,5,6-pentahydroxycyclohexyl. Compounds in which $R^4$ and $R^5$ each represent alkylcarbonyl are preferred. Also preferred are compounds in which $R^6$ represents 2-(trimethylammonium)ethyl, compounds of this type being known as lecithins, and those compounds in which $R^4$ and $R^5$ each represent alkylcarbonyl having, say, 8 to 16 carbon atoms or having, say, 12 to 16 carbon atoms, and in which $R^6$ represents 2-(trimethylammonium)ethyl, in particular those compounds in which $R^4$ and $R^5$ each represent octanoyl.

Also suitable as surface-active substances are compounds of the formula $R^7$—[—O—$CH_2$—$CH_2$—O]$_p$—H (VI), in which $R^7$ denotes a saturated or olefinically unsaturated hydrocarbon group having 8 to 15 carbon atoms, and p denotes an integer from 2 to 25. These compounds are generally added in an amount of 0.2 to 200 mg/l. $R^7$ is preferably ($C_{12}$ or $C_{13}$)-alkyl, and p is preferably 4 to 23, in particular 6 to 15.

The folding conditions used in the process according to the invention are generally those described in European Pat. No. 37 255. This means that it is generally carried out at a temperature of 0° to 37° C., with 1 to 5 —SH units per —$SSO_3^-$ group, in a pH range from 7 yo 11.5, and with a S-sulfonate insulin precursor concentration of up to 10 mg per ml of aqueous medium. Preferred mercaptans are are 2-mercaptoethanol, thioglycolic acid and its methyl ester, 3-mercapto-1,2-propanediol and 3-mercaptopropionic acid and its esters. Preferred reaction conditions are a concentration of 0.2 to 1 mg/ml S-sulfonate insulin precursor, a pH range from 9.5 to 11, a reaction temperature of 2° to 10° C., a reaction time of 5 to 20 hours, and a ratio of —SH to —$SSO_3^-$ group of 2-3. For practical reasons, it is also preferred to exclude oxygen to a large extent, although this is by no means necessary.

The pH is advantageously changed by addition of dilute mineral acids, such as hydrochloric, sulfuric or phosphoric acid, but it is also possible to use organic acids which do not react with the insulin precursors, such as acetic acid, or acidic salts such as phosphates.

The precipitate obtained when the pH is changed can readily be removed by centrifugation. It is to a large extent converted back into the S-sulfonate form by direct sulfitolysis as described, for example, Swan in Nature 180, 643–645 (1957). This form can then, if necessary, be purified by chromatographic processes, and then, for example, converted in the manner indicated above, advantageously in the presence of a small quantity of a physiologically acceptable surface-active substance of the type mentioned, into the folded insulin precursor. However, it can also be processed in accordance with a further embodiment, namely by adding a surface-active substance of the abovementioned type to the partially linked insulin precursors, which have been prepared with a small excess of mercaptan, bubbling oxygen, for example atmospheric oxygen, through the solution, and thus effecting the reoxidation.

The surface-active substance prevents denaturation of the insulin precursor, for example on the gas bubbles, during this.

Thus, it is possible by the process according to the invention to increase the folding yield, including the recovery of false recombinants, to 80 or even to 90%.

EXAMPLES

1. Preparation of human preproinsulin from preproinsulin S-sulfonate 1.2 g of preproinsulin S-sulfonate with the presequence R=Gly—Asn—Ser—Ala—Arg— and the sequence of human proinsulin were dissolved in 2.5 l of 50 mM degassed glycine buffer of pH 10.6, and stirred gently with 147 μl of mercaptoethanol at 4° C. overnight. According to high-pressure liquid chromatography (high performance liquid chromatography=HPLC) analysis, the folding yield in the medium was 0.32 mg/ml (67%) and, using *Staphylococcus aureus* (protease V8) fingerprint, it was found that the A7-B7 disulfide bridge is present to the extent of 65% and the B19-A20 disulfide bridge is present to the extent of 93%. The fingerprint analysis was carried out as follows: 0.1 units of *S. aureus* protease V8 were added to 200 μl of a solution of 0.5 mg/ml of the insulin precursor in 50 mM tris(hydroxymethyl)methylammonium chloride(tris) pH 7.5, and the solution was incubated at 37° C. for 30 minutes. An aliquot of the solution is then directly analyzed in the HPLC. The HPLC analysis was carried out on C18 reversed phase with a linear gradient from 20 to 45% B. Buffer A which was used was 0.05M tetraethylammonium phosphate, 0.25M sodium perchlorate and 10% acetonitrile in the total phase (pH 3). Buffer B which was used was 0.05M tetraethylammonium phosphate with 90% acetonitrile in the total phase (pH 3). The abovementioned figures of 65 and 93% were determined from the ratio of the fragment peaks appearing at about 7, 10 and 14 minutes, and by comparing with a human proinsulin standard.

The solution was brought to pH 9, and 25 mg of surface-active polyethylene/polypropylene glycol were added. Then, at 4° C., about 50 l of oxygen were bubbled through, with stirring, for one hour.

The solution was brought to pH 5.4 with 1N HCl, the turbidity which appeared being removed by centrifugation. The precipitate was washed with acetone and diethyl ether or methyl tert.-butyl ether and dried. Weight: 520 mg. Natural preproinsulin was precipitated from the clear supernatant by addition of 250 g of NaCl at pH 3. Yield: 720 mg (60%).

The precipitate formed at pH 5.4 was sulfitolyzed in 100 ml of 7M urea solution containing 800 mg of sodium sulfite and 600 mg of sodium tetrathionate at pH 7.6 and 4° C., and the reaction product was precipitated by dialysis against aqueous buffer (pH 3). The dried precipitate weighed 540 mg, the quantity of recovered preproinsulin S-sulfonate being 382 mg. The latter was reduced with 40 µl of mercaptoethanol as indicated above, a further 226 mg of natural preproinsulin being produced yield in this particular stage 59%), so that the cumulative folding yield was 946 mg, corresponding to 78.8%.

In a second, analogous repetition, a further 78 mg (individual yield in the third stage 54%) of natural preproinsulin were obtained by precipitation at pH 5.4 from the 144 mg produced in the first repetition. The cumulative yield of natural preproinsulin was now 1.024 g, corresponding to 85.3%.

2. Refolding of porcine proinsulin 0.4 g of porcine proinsulin S-sulfonate was dissolved in 800 ml of 50 mM glycine buffer of pH 10.5 and at about 4° C., and the solution was degassed and 49.1 mg of thioglycolic acid were added. The solution was stirred gently at 4° C. overnight. The solution was then adjusted to pH 5.2 with 4N HCl, a precipitate being produced. The latter was removed by centrifugation, washed with acetone and dialkyl ether, and dried. Weight: 115 mg. The clear supernatant contained, according to HPLC, 239 mg (yield 60%) of proinsulin.

The precipitate was sulfitolyzed as described in Example 1, this producing 120 mg, from which 88 mg of proinsulin S-sulfonate were obtained in accordance with the above-mentioned treatment. The latter were refolded with 12.3 mg of thioglycolic acid in analogy to the first stage. At pH 5.2 there was formation of a slight turbidity which, after centrifugation, provided a further 43 mg of dry material.

The supernatant which was obtained on centrifugation and which contained 55 mg of proinsulin (62% yield, corresponding to 73.5% cumulative yield) was combined with the supernatant obtained at pH 5.2 in the first stage (1.0 l). 6 g of tris were added, the pH was adjusted to 7.2, and 0.6 U of trypsin and 6 U of carboxypeptidase B were added. The solution was stirred gently at 25° C., and the progress of the reaction was followed by HPLC. After about 3–4 hours, the proinsulin had completely disappeared and been replaced by C-peptide and porcine insulin.

The reaction was terminated by addition of 40 ml of 1% strength $ZnCl_2$ solution and adjustment to pH 5.4. A flocculant precipitate resulted and could easily be centrifuged and was composed to a large extent of porcine insulin. Yield 201 mg (91% based on refolded proinsulin used). Final purification of the porcine insulin thus isolated was carried out by customary processes, for example on ion exchangers.

I claim:

1. A process for the preparation of correctly-recombined insulin precursors of the formula (I)

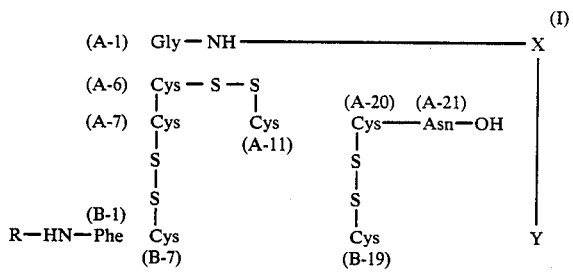

in which R is hydrogen or the presequence $P_m—Q_n—$, in which P is a sequence of naturally occurring amino acids with m being from 0 to 50, Q are basic natural amino acids, and n is an integer from 1 to 4, Y represents $—Lys^{B29}—Z^{B30}—$, in which Z denotes Ala, Thr or Ser, and the bridge extending from A-1 to A-21 is an insulin A-chain, the bridge extending from B-1 to B-30 represents an insulin B-chain, and X is a bridge which is bonded to the insulin A-chain at the amino group of A-1 and is bonded to the insulin B-chain at the ε-amino group of B-29—in which case it is bonded to the free bond of $Z^{B30}OH$—or at the carboxyl group of B-30, comprising the steps of folding, in a reaction mixture, S-sulfonates of the formula (II)

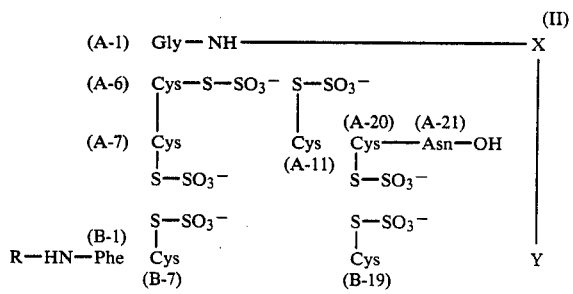

in which R, X and Y have the abovementioned meanings, under conditions sufficient to correctly recombine the insulin precursors of formula (I), precipitating false recombinants co-formed in the folding step by adjustment of the reaction mixture to pH 4 to 6, removing the precipitate, converting the precipitate by sulfitolysis into S-sulfonates of the formula (II), and subjecting the sulfitolyzed S-sulfonates to folding under conditions sufficient to form the insulin precursors of formula (I).

2. The process as claimed in claim 1, wherein the reaction mixture contains, when the precipitate is formed, a physiologically acceptable surface-active substance effective to prevent the binding of correctly-recombined insulin precursors of formula (I) to co-formed false recombinants.

3. The process as claimed in claim 2, wherein the surface-active substance is a polymer of the formula $R^2—O—X_n—R^3$ (III), in which $X_n$ is a chain of n members of the formula

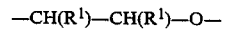

$$—CH(R^1)—CH(R^1)—O— \qquad (IV),$$

n is 2 to 80, preferably 15 to 45, and $R^1$ is hydrogen, methyl or ethyl, and $R^2$ and $R^3$ being, independently of one another, hydrogen or an organic radical, but with the proviso that the compounds III contain at least 12 carbon atoms.

4. The process as claimed in claim 3, wherein the polymer is added in an amount of 1 to 400, preferably 2 to 200 mg/l.

5. The process as claimed in claim 1, wherein the folding step is carried out in the presence of a physiologically acceptable surface-active substance effective to prevent the binding of correctly-recombined insulin precursors of formula (I) to co-formed false recombinants.

6. The process as claimed in claim 5, wherein an excess of mercaptan is used in the folding, and the recombined insulin precursors are reoxidized with oxygen.

7. The process as claimed in claim 2, wherein the folding step is carried out in the presence of a physiologically acceptable surface-active substance effective to prevent the binding of corectly-recombined insulin precursors of formula (I) to co-formed false recombinants.

8. The process as claimed in claim 3 wherein the folding step is carried out in the presence of a physiologically acceptable surface-active substance effective to prevent the binding of correctly-recombined insulin precursors of formula (I) to co-formed false recombinants.

9. The process as claimed in claim 4 wherein the folding step is carried out in the presence of a physiologically acceptable surface-active substance effective to prevent the binding of correctly-recombined insulin precursors of formula (I) to co-formed false recombinants.

10. The process as claimed in any one of claims 1, 2, 3, 4, 5 or 6 wherein the folding is carried out using a ratio of —SH groups to —$SO_3^-$ groups of 1 to 5, in an aqueous medium, at a pH of 7 to 11.5 and a S-sulfonate insulin precursor concentration of up to 10 mg per ml, and at a temperature of 0° to 37° C.

11. The process as claimed in claim 7, further comprising at least one of the following process modifications: the reaction is carried out (1) with a S-sulfonate insulin precursor concentration of 0.2 to 1 mg per ml of aqueous medium, (2) at a pH of 9.5 to 11, (3) at a reaction temperature of 2° to 10° C., (4) with a reaction time of 5 to 20 hours, (5) using a ratio of —SH groups to —$SO_3^-$ groups of 2 to 3, and (6) with exclusion of oxygen to a large extent.

12. The process as claimed in any one of claims 1, 2, 3, 4, 5 or 6 wherein the mercaptan is 2-mercaptoethanol, thioglycolic acid or its methyl ester, 3-mercapto-1,2-propane-diol or 3-mercaptopropionic acid or its esters.

* * * * *